United States Patent [19]

Marquardt et al.

[11] Patent Number: 5,304,375
[45] Date of Patent: Apr. 19, 1994

[54] SPERMICIDAL COATING COMPOSITION

[75] Inventors: Gerwig Marquardt, Odenthal; Peter Preiss, Wuppertal, both of Fed. Rep. of Germany

[73] Assignee: Bayer Aktiengesellschaft, Leverkusen, Fed. Rep. of Germany

[21] Appl. No.: 695,854

[22] Filed: May 6, 1991

[30] Foreign Application Priority Data

May 15, 1990 [DE] Fed. Rep. of Germany ....... 4015543

[51] Int. Cl.$^5$ ............................................. A01N 25/00
[52] U.S. Cl. ............................ 424/405; 424/DIG. 14
[58] Field of Search ................... 424/78, DIG. 14, 405

[56] References Cited

U.S. PATENT DOCUMENTS

| 4,326,510 | 4/1982 | Buckles | 424/430 |
| 4,814,184 | 3/1989 | Aguadisch et al. | 424/425 |
| 4,999,342 | 3/1991 | Ahmad et al. | 514/841 |
| 5,019,604 | 5/1991 | Lemole | 424/81 |
| 5,035,890 | 7/1991 | Braun | 424/401 |

FOREIGN PATENT DOCUMENTS 0328421 2/1989 European Pat. Off. .
8904647 6/1989 PCT Int'l Appl. .

OTHER PUBLICATIONS

Derwent Publications Ltd., Week 8742 of AN 87-294036.

Primary Examiner—Thurman K. Page
Assistant Examiner—Peter F. Kulkosky
Attorney, Agent, or Firm—Sprung Horn Kramer & Woods

[57] ABSTRACT

The present invention relates to spermicidal coating compositions for coating latex materials containing one or more spermicidal agents, more particularly based on Nonoxinol-9, and one or more organopolysiloxane compounds in which the spermicidal agents are soluble.

3 Claims, No Drawings

SPERMICIDAL COATING COMPOSITION

BACKGROUND OF THE INVENTION

This invention relates to silicone-based coating compositions for the treatment of latex materials, particularly condoms and similar articles, which possess the advantage and characteristic that spermicidal agents are soluble in such compositions.

Latex materials are used for various applications, including the field of hygiene, for example as protective gloves, covers, protection for bandages, but especially for condoms.

In view of the growing risk of AIDS diseases, condoms are attracting increasing attention as protectives and prophylactics.

On the evidence of scientific investigations, the use of a condom as a genital HIV prophylactic affords the best possible protection at the present time (cf. Knut O. K. Hoffmann: Wie sicher ist das Kondom ? (How Safe is the Condom ?), ZFA 7/1988).

The industrial manufacture of the condom for around 65 years is attributable to Julius Fromm and has now reached a high standard in regard to the material quality of these articles. Latex is almost exclusively used for the production of condoms, being distinguished above all by its enormous tear strength, elasticity and imperviousness.

In addition, latex-based condoms can readily be produced in extremely thin layers having a thickness of the order of 0.08 mm. On account of the relatively poor slip properties of latex, a lubricant is generally applied after the production of these articles to minimize problems in use.

Whereas, previously, solid materials, such as talcum, were used, oil-like products are today mostly used for improving slip properties.

Several different lubricants or preparations are described in the patent literature, with particular significant advantages being attributed mainly to the glycols and classical methyl silicone oils.

For example, Japanese patent application JP 52 138 397 describes the use of fine glass microspheres in combination with silicone oil, various glycols, glycerol or modified alcohols, while JP 70 006 119 describes a system of silicone oil and pteridophyta spores.

In addition, JP 59 141 942 mentions silicone oils or water-soluble polymers for improving slip properties.

Combinations of modified alcohols, alginates, propylene glycol, gelatine, sodium chloride and saccharides (JP 74 019 799) and polyethylene glycol in combination with silicone oils (JP 62 164 460) have been described with particular regard to the spermicidal treatment of the lubricants.

Of the large number of useable systems, methyl silicone oils (PDMS) of medium viscosity are now preferably used as wet coating compositions because, by virtue of their high compatibility with mucous membrane, their favorable slip properties and their compatibility with latex, they afford advantages over glycols or other hydrophilic systems. In addition, PDMS are materials which are not contaminated by bacteria and, if properly used, may be regarded as extremely low in germs.

On account of the growing risk of possible infection with the HIV virus through sexual intercourse, greater importance than before is now being attributed to coating compositions which inhibit in vivo the activity of reverse transcriptase in HIV replication. From studies conducted by Hicks (cf. "Inactivation of HIV-III/LAV-infected cultures of normal human lymphocytes by Nonoxinol-9 in vitro", Lancet II, 1422-1423, 1985), it is known that such activity is observed in the case of spermicidal substances, for example of the Nonoxinol-9 type, a nonionic, surface-active substance.

Now, it would be desirable if substances such as these were soluble in the silicone oils hitherto used, although this is unfortunately not the case on account of the difference in chemical structure between the two classes of compounds.

Nonoxinol-9 has the chemical name 26-(4-nonylphenoxy)-3,6,9,12,15,18,21,24-octaoxahexacosan-1-ol and, in the broadest sense, is thus a modified polyether which is compatible with or soluble in glycols, polyglycols or polyethers.

Accordingly, glycol, polyglycol or a glycol-like system is almost exclusively used as carrier for Nonoxinol-9 for the spermicidal treatment of condoms. These hydrophilic substances generally show relatively poor wettability of the condom surface and less well pronounced compatibility with latex. In addition, they make the condom more tacky by comparison with PDMS.

The problem addressed by the present invention is to use silicone systems having solubility properties for active substances based on nonoxinol, preferably Nonoxinol-9, for the treatment of condoms to enable storable coating compositions with spermicidal activity to be produced.

In addition, these coating compositions would be fairly similar to PDMS in their properties, such as slip, tackiness and compatibility with mucous membrane.

DESCRIPTION OF THE PREFERRED EMBODIMENTS

Accordingly, the present invention relates to spermicidal coating compositions for coating latex materials containing one or more spermicidal agents, more particularly based on Nonoxinol-9, and one or more organopolysiloxane compounds in which the spermicidal agents are soluble.

The solubility problems encountered heretofore have been solved in particular by the use of hydroxyalkylated siloxanes having the following structures:

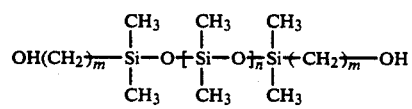

wherein, m=1-3, n=1-20 and, on the other hand, also by the use of a class of linear or branched polyether/polysiloxane copolymers. The basic structure of these latter compounds may be represented by the following three formulae:

Type 1

Lateral attachment of the polyether function to the linear siloxane

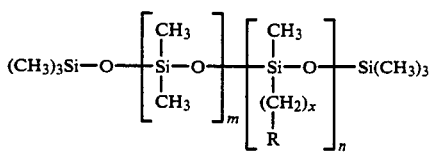

wherein, R=polyether, x=0-3, m=0-30, n=1-30

Type 2

Terminal attachment of the polyether function to the linear siloxane

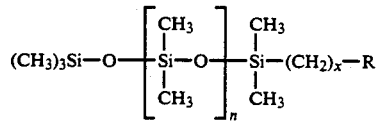

wherein, R=polyether, x=0-3, n=0-30

Type 3

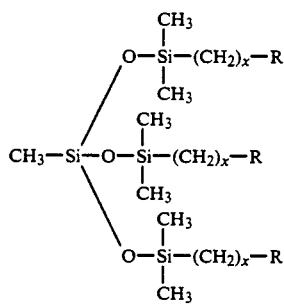

wherein, R=polyether, x=0-3.

In principle, other polyether/polysiloxane copolymers having modified structures may also be used for the preparation of the coating compositions according to the invention.

Hydroxyalkylated siloxanes may be prepared, for example, from chloromethyl chlorosilane, reaction to dihydroxymethyl tetramethyl disiloxane and equilibration with octamethyl cyclotetrasiloxane.

Starting products for the preparation of polyether/polysiloxane copolymers are polysiloxanes which contain reactive groups, such as ≡SiCl, ≡SiOR or ≡SiH, within the polymer chain (lateral) or at its ends (terminal). These prepolymers are obtained either by hydrolysis of methyl chlorosilanes or by copolymerization of cyclic or linear polymethyl siloxanes with functional siloxanes. In both processes, the next step is an equilibration reaction in which the dimethyl siloxy groups and the functional siloxy groups are brought into the statistical equilibrium using acidic catalysts by breaking up and relinking of the Si—O—Si bonds. The reaction of these reactive siloxanes with polyethers then leads to polyether/polysiloxane copolymers.

Both described classes of compounds have long been known (for example from Walter Noll: Chemie und Technologie der Silicone, 2nd Edition, 1968, Verlag Chemie GmbH, Weinheim/Bergstraße) and, depending on their structure, are used as surface-finishing products for natural and artificial leather, as foam stabilizers in the processing of PU, as surfactants and as antistatic agents and also as skin-compatible components in various dermatological and cosmetic formulations. Despite their many and varied uses, no negative dermatological effects have hitherto been observed during their processing.

The effectiveness of the classes of compounds according to the invention is demonstrated in the following Examples.

EXAMPLES

Example 1

0.3 g of a solution consisting of 6 parts by weight Nonoxinol-9 and 94 parts by weight $\alpha,\gamma$-hydroxymethyl dimethylsilyl polydimethyl siloxane containing 12 dimethyl silyloxy units were applied dropwise to the top of a rolled latex condom. The article thus treated was then sealed and stored for a few days at room temperature. During this period, the spreading properties of the silicone resulted in complete coverage of the condom surface with the coating composition containing the spermicidal agent. Subsequent haptic testing of the treated article revealed a distinct improvement in the slip properties by comparison with untreated material together with only very slightly noticeable tackiness. Testing of the mechanical properties of condoms which had been stored in the coating composition used for 14 days at 50° C. did not suggest any change in the quality of the latex, even after prolonged contact with the silicone preparation.

Example 2

0.5 g of a solution consisting of 6 parts by weight Nonoxinol-9, 20 parts by weight decamethyl cyclopentasiloxane and 74 parts by weight of a branched polyether/polysiloxane copolymer of type 3 with x=1 and a 75% polyether component consisting of ethoxy and propoxy units were applied to the surface of a condom and tested as in Example 1. The haptic tests again showed favorable slip behaviour and minimal tackiness. There was no evidence of any mechanical change in the duality of the latex after storage.

Example 3

0.4 g of a solution consisting of 6 parts by weight Nonoxinol-9 and 94 parts by weight of a linear polyether/polysiloxane copolymer of type 1 with m=10, n=1, x=3 and a 60% laterally attached polyether component consisting of ethoxy and propoxy units was applied to the surface of a condom as in Example 1 and the article thus treated was subsequently tested. The haptic tests showed favorable slip properties and very slight tackiness. There was no evidence of any mechanical change in the quality of the latex after storage.

Example 4

0.4 g of a solution consisting of 6 parts by weight Nonoxinol-12 and 94 parts by weight of a linear polyether/polysiloxane copolymer of type 1 with m=10, n=1, x=3 and a 60% laterally attached polyether component consisting of ethoxy and propoxy units was applied to the surface of a condom as in Example 1 and the article thus treated was subsequently tested. The haptic tests showed favorable slip properties and very slight tackiness. There was no evidence of any mechanical change in the quality of the latex after storage.

Example 5

0.3 g of a solution consisting of 6 parts by weight Nonoxinol-9 and 94 parts by weight of a linear polyether/polysiloxane copolymer of type 2 with $n=12$ and $x=3$ and a 50% terminally attached polyether component consisting of ethoxy and propoxy units was applied to the surface of a condom as in Example 1 and the article thus treated was subsequently tested. The haptic tests again showed very favorable slip properties together with slight tackiness. As in the preceding Examples, there was no evidence of any mechanical change in the quality of the latex after storage.

It is understood that the specification and examples are illustrative but not limitative of the present invention and that other embodiments within the spirit and scope of the invention will suggest themselves to those skilled in the art.

What is claimed is:

1. A spermicidal coating composition for coating latex materials consisting essentially of Nonoxinol-9 as the spermicidal agent, and further characterized in that it contains organopolysiloxane compounds having hydroxyalkyl groups or polyether functions attached to Si wherein the hydroxyalkyl group functionality or polyether alkoxy chain length of said organopolysiloxane is such as to solubilize Nonoxyinol-9 without turididity.

2. A coating method in which a coating composition according to claim 1 is used for coating latex membrane articles.

3. A coating method in which a coating composition according to claim 1 is used for coating condoms.

* * * * *